United States Patent
Shin (10) Patent No.: US 10,188,338 B2
(45) Date of Patent: Jan. 29, 2019

(54) CONTENT EVALUATION SYSTEM AND CONTENT EVALUATION METHOD USING THE SYSTEM

(71) Applicant: NHN Entertainment Corporation, Seongnam-si (KR)

(72) Inventor: Kyung Soon Shin, Seongnam-si (KR)

(73) Assignee: NHN Entertainment Corporation, Seongnam-si (KR)

( * ) Notice: Subject to any disclaimer, the term of this patent is extended or adjusted under 35 U.S.C. 154(b) by 5 days.

(21) Appl. No.: 15/462,205

(22) Filed: Mar. 17, 2017

(65) Prior Publication Data

US 2017/0188929 A1 Jul. 6, 2017

Related U.S. Application Data

(62) Division of application No. 14/484,935, filed on Sep. 12, 2014.

(30) Foreign Application Priority Data

Sep. 13, 2013 (KR) ........................ 10-2013-0110301

(51) Int. Cl.
*A61B 5/00* (2006.01)
*A61B 5/0476* (2006.01)
(Continued)

(52) U.S. Cl.
CPC .......... *A61B 5/165* (2013.01); *A61B 5/02055* (2013.01); *A61B 5/0478* (2013.01);
(Continued)

(58) Field of Classification Search
None
See application file for complete search history.

(56) References Cited

U.S. PATENT DOCUMENTS 3,735,753 A * 5/1973 Pisarski ............... A61B 5/0478
600/383
4,846,190 A * 7/1989 John .................. A61B 5/04021
600/544
(Continued)

FOREIGN PATENT DOCUMENTS

CN 101631496 1/2010
CN 101711388 5/2010
(Continued)

OTHER PUBLICATIONS

Final Office Action dated Jul. 12, 2017, in U.S. Appl. No. 14/484,935.
(Continued)

*Primary Examiner* — Carl H Layno
*Assistant Examiner* — Manolis Pahakis
(74) *Attorney, Agent, or Firm* — H.C. Park & Associates, PLC (57) ABSTRACT

A reliable content evaluation method and system are disclosed. The system includes a brainwave detector, a bio signal detector, a first controller, and a second controller. The brainwave detector detects a brainwave signal of a subject provided with content and outputs a result. The bio signal detector detects bio signals of the subject and outputs a result. The first controller can modify the brainwave and the bio signals to a signal level available for the second controller. The second controller detects change of the brainwave signal and the bio signal through an analysis of the brain wave signal and the bio signal from the first controller. Then, the second controller determines at least one of a degree of engagement and an emotional reaction of the subject to the content, using changes in the brainwave signal and the bio signal, and evaluates the content using the determined results.

9 Claims, 7 Drawing Sheets

(51) Int. Cl.

| | | |
|---|---|---|
| *A61B 5/0484* | (2006.01) | |
| *A61B 5/16* | (2006.01) | |
| *A61B 5/0478* | (2006.01) | |
| *A61B 5/0205* | (2006.01) | |
| *G06Q 30/02* | (2012.01) | |
| *G07F 17/32* | (2006.01) | |
| *A61B 5/0496* | (2006.01) | |
| *A61B 5/11* | (2006.01) | |
| *A61B 5/0488* | (2006.01) | |
| *A61B 5/053* | (2006.01) | |
| *A61B 5/024* | (2006.01) | |
| *A61B 5/01* | (2006.01) | |
| *A61B 5/08* | (2006.01) | |

(52) U.S. Cl.
CPC ........ *A61B 5/04842* (2013.01); *A61B 5/6803* (2013.01); *A61B 5/721* (2013.01); *G06Q 30/02* (2013.01); *G06Q 30/0242* (2013.01); *G07F 17/3206* (2013.01); *A61B 5/01* (2013.01); *A61B 5/024* (2013.01); *A61B 5/0488* (2013.01); *A61B 5/0496* (2013.01); *A61B 5/04845* (2013.01); *A61B 5/0533* (2013.01); *A61B 5/08* (2013.01); *A61B 5/0816* (2013.01); *A61B 5/1103* (2013.01); *A61B 5/7235* (2013.01)

(56) References Cited

U.S. PATENT DOCUMENTS

| | | | | |
|---|---|---|---|---|
| 5,676,138 | A * | 10/1997 | Zawilinski | A61B 3/113 128/905 |
| 5,724,987 | A * | 3/1998 | Gevins | A61B 5/0484 600/544 |
| 5,772,591 | A * | 6/1998 | Cram | A61B 5/4041 600/383 |
| 5,983,129 | A * | 11/1999 | Cowan | A61B 5/04842 128/905 |
| 6,236,885 | B1 * | 5/2001 | Hunter | A61B 5/0484 600/28 |
| 6,293,904 | B1 * | 9/2001 | Blazey | A61B 5/16 434/236 |
| 6,487,444 | B2 * | 11/2002 | Mimura | A61B 5/04842 600/300 |
| 6,585,521 | B1 * | 7/2003 | Obrador | G09B 23/28 369/27.01 |
| 7,113,916 | B1 * | 9/2006 | Hill | G06Q 30/02 705/7.32 |
| 7,120,880 | B1 * | 10/2006 | Dryer | G06Q 30/02 715/863 |
| 8,939,903 | B2 * | 1/2015 | Roberts | A61B 5/165 600/300 |
| 9,191,450 | B2 * | 11/2015 | Sidi | G06Q 30/02 |
| 2001/0031916 | A1 * | 10/2001 | Bennett | A61B 5/0492 600/383 |
| 2002/0182574 | A1 * | 12/2002 | Freer | A61B 5/0482 434/236 |
| 2002/0188216 | A1 * | 12/2002 | Kayyali | A61B 5/04085 600/544 |
| 2007/0055169 | A1 * | 3/2007 | Lee | A61B 5/0006 600/544 |
| 2008/0091512 | A1 | 4/2008 | Marci et al. | |
| 2008/0214902 | A1 | 9/2008 | Lee et al. | |
| 2008/0221400 | A1 | 9/2008 | Lee et al. | |
| 2008/0221472 | A1 * | 9/2008 | Lee | A61B 5/0476 600/544 |
| 2008/0221969 | A1 * | 9/2008 | Lee | A61B 5/04842 600/544 |
| 2008/0222671 | A1 | 9/2008 | Lee et al. | |
| 2008/0255949 | A1 * | 10/2008 | Genco | A61B 5/0205 705/14.4 |
| 2009/0030287 | A1 * | 1/2009 | Pradeep | G06Q 30/02 600/300 |
| 2009/0063255 | A1 * | 3/2009 | Pradeep | G06Q 30/02 705/7.29 |
| 2009/0088610 | A1 * | 4/2009 | Lee | A61B 5/16 600/301 |
| 2010/0004977 | A1 * | 1/2010 | Marci | G06Q 10/10 705/7.32 |
| 2010/0094702 | A1 * | 4/2010 | Silberstein | A61B 5/04012 705/14.43 |
| 2011/0046504 | A1 * | 2/2011 | Pradeep | A61B 5/04842 600/544 |
| 2011/0105857 | A1 | 5/2011 | Zhang et al. | |
| 2012/0030696 | A1 * | 2/2012 | Smith | G06Q 30/02 725/10 |
| 2012/0130800 | A1 | 5/2012 | Pradeep et al. | |
| 2012/0259240 | A1 * | 10/2012 | Llewellynn | G06Q 30/02 600/558 |
| 2013/0185140 | A1 | 7/2013 | Pradeep et al. | |
| 2014/0207558 | A1 | 7/2014 | Silberstein | |
| 2015/0080675 | A1 * | 3/2015 | Shin | A61B 5/165 600/301 |
| 2015/0157255 | A1 * | 6/2015 | Nduka | A61B 5/165 600/301 |
| 2015/0213019 | A1 * | 7/2015 | Marvit | G06Q 30/0242 707/748 |
| 2016/0110737 | A1 * | 4/2016 | Villareal | G06Q 30/0203 705/7.32 |

FOREIGN PATENT DOCUMENTS

| | | |
|---|---|---|
| CN | 101720200 | 6/2010 |
| CN | 101755406 | 6/2010 |
| JP | 06-076044 | 3/1994 |
| JP | 07-075631 | 3/1995 |
| JP | 09-262216 | 10/1997 |
| JP | 2005-034620 | 2/2005 |
| JP | 2005-056205 | 3/2005 |
| JP | 2005-293209 | 10/2005 |
| JP | 2007-130212 | 5/2007 |
| JP | 2008-205861 | 9/2008 |
| JP | 2010-503109 | 1/2010 |
| JP | 2011-505175 | 2/2011 |
| JP | 2011-182843 | 9/2011 |
| JP | 2011-189081 | 9/2011 |
| JP | 2012-059107 | 3/2012 |
| JP | 2012-160173 | 8/2012 |
| JP | 2012-183292 | 9/2012 |
| KR | 10-2012-0113572 | 10/2012 |
| WO | 2008/030493 | 3/2008 |
| WO | 2009/059246 | 5/2009 |
| WO | 2010/001512 | 1/2010 |

OTHER PUBLICATIONS

Mike Ambinder, "Valve's Approach to Playtesting: the Application of Empiricism", Game Developers Conference, Mar. 2009.

Non-Final Office Action dated May 14, 2018, in U.S. Appl. No. 14/484,935.

* cited by examiner

CONTENT EVALUATION SYSTEM AND CONTENT EVALUATION METHOD USING THE SYSTEM

CROSS REFERENCE TO RELATED APPLICATION

This application is a Divisional of U.S. patent application Ser. No. 14/484,935, filed on Sep. 12, 2014, and claims priority from and the benefit of Korean Patent Application No. 10-2013-0110301, filed on Sep. 13, 2013, each of which is hereby incorporated by reference for all purposes as if fully set forth herein.

BACKGROUND

Field

Exemplary embodiments of the present disclosure relate to a content evaluation system to evaluate content such as games, movies, advertisements, and music, and a content evaluation method using the system.

Discussion of the Background

In recent years, researchers have studied the economic impact of content generated and provided through various means (e.g., Internet, cameras, television, advertisements, etc.). Certain factors, such as the economics (e.g., revenue generated by the provided content) or strategy to deploy the content (e.g., timing of deployment) are being assessed in greater detail.

Generally, assessment of content is done by people who have been provided with the content via a survey. Content assessment via a survey is generally done after development of the contents. However, survey results are very subjective, inconsistent, and unreliable because the survey results may depend on the emotional state or memories of the people surveyed.

Accordingly, a more objective and reliable content evaluation method is needed.

The above information disclosed in this Background section is provided to enhance understanding of the background of the disclosed subject matter and therefore may contain information that does not form any part of the prior art nor what the prior art may suggest to a person of ordinary skill in the art.

SUMMARY

Exemplary embodiments of the present disclosure provide a content evaluation method and system.

Additional features of the present disclosure will be set forth in the description which follows, and in part will be apparent from the description, or may be learned by practice of the disclosed subject matter.

Exemplary embodiments of the present disclosure disclose a content evaluation system including a brainwave detector, a bio signal detector, and a controller. The brainwave detector detects a brainwave signal of a subject provided with content. The bio signal detector detects a bio signal of the subject provided with the content. The controller receives the brainwave signal from the brainwave detector and the bio signal from the bio signal detector. The controller determines a change in the brainwave signal and a change in the bio signal. Then, the controller determines a degree of engagement and an emotional reaction of the subject to the content using the change of the brainwave signal and the change of the bio signal, and evaluates the content using at least one of the degree of the engagement and the emotional reaction.

Exemplary embodiments of the present disclosure disclose a method of evaluating content. The method includes detecting a brainwave signal of a subject provided with the content, detecting a bio signal of the subject, detecting a change of the brainwave signal, detecting a change of the bio signal, determining a degree of engagement and an emotional reaction of the subject to the content using the change in the brainwave signal and the change in the bio signal, and evaluating the content using at least one of the degree of engagement and the emotional reaction.

It is to be understood that both the foregoing general description and the following detailed description are exemplary and explanatory and are intended to provide further explanation of the disclosed subject matter as claimed.

BRIEF DESCRIPTION OF THE DRAWINGS

The accompanying drawings, which are included to provide a further understanding of the disclosed subject matter and are incorporated in and constitute a part of this specification, illustrate embodiments of the disclosed subject matter, and together with the description serve to explain the principles of the disclosed subject matter.

DETAILED DESCRIPTION OF THE ILLUSTRATED EMBODIMENTS

Exemplary embodiments of the disclosed subject matter are described more fully hereinafter with reference to the accompanying drawings. The disclosed subject matter may, however, be embodied in many different forms and should not be construed as limited to the exemplary embodiments set forth herein. Rather, the exemplary embodiments are provided so that this disclosure is thorough and complete, and will convey the scope of the disclosed subject matter to those skilled in the art. In the drawings, the size and relative sizes of layers and regions may be exaggerated for clarity. Like reference numerals in the drawings denote like elements.

It will be understood that when an element or layer is referred to as being "on," "connected to," or "coupled to" another element or layer, it can be directly on, connected, or coupled to the other element or layer or intervening elements or layers may be present. In contrast, when an element is referred to as being "directly on," "directly connected to," or "directly coupled to" another element or layer, there are no intervening elements or layers present. As used herein, the term "and/or" includes any and all combinations of one or more of the associated listed items. It may also be understood that for the purposes of this disclosure, "at least one of X, Y, and Z" can be construed as X only, Y only, Z only, or any combination of two or more items X, Y, and Z (e.g., XYZ, XYY, YZ, ZZ).

It will be understood that, although the terms first, second, and third, etc. may be used herein to describe various elements, components, regions, layers, and/or sections, these elements, components, regions, layers and/or sections should not be limited by these terms. These terms are only used to distinguish one element, component, region, layer or section from another region, layer or section. Thus, a first element, component, region, layer, or section discussed below could be termed a second element, component, region, layer or section without departing from the teachings of the disclosed subject matter.

Spatially relative terms, such as "beneath," "below," "lower," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the disclosed subject matter. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the disclosed subject matter are described herein with reference to cross-sectional illustrations that are schematic illustrations of idealized example embodiments (and intermediate structures) of the disclosed subject matter. As such, variations from the shapes of the illustrations as a result, for example, of manufacturing techniques and/or tolerances, are to be expected. Thus, example embodiments of the disclosed subject matter should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change or transition from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the disclosed subject matter.

Unless otherwise defined, all terms (including technical and scientific terms) used herein have the same meaning as commonly understood by one of ordinary skill in the art to which this disclosed subject matter belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the disclosed subject matter will be described in detail with reference to the accompanying drawings.

Figure 1:
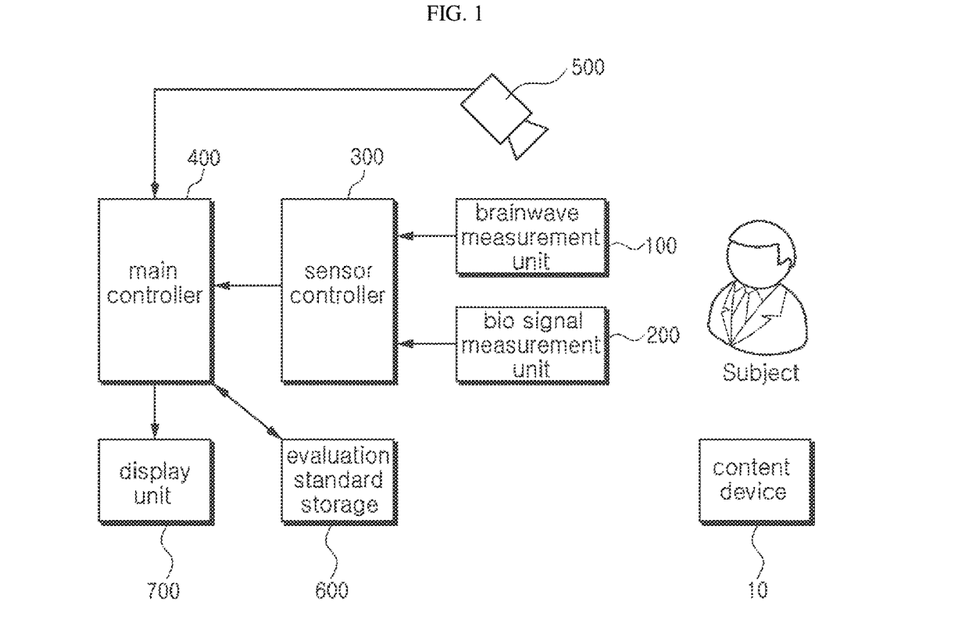
FIG. 1 is a block diagram showing a content evaluation system according to exemplary embodiments of the present disclosure.

FIG. 1 is a block diagram showing a content evaluation system according to exemplary embodiments of the disclosed subject matter.

Referring to FIG. 1, a content evaluation system may evaluate content provided to a subject through a content device 10. The content evaluation system may include a brainwave detector 100, a bio signal detector 200, a first controller 300, a second controller 400, a camera 500, an evaluation standard data storage 600, and a display 700. The content may include, but is not limited to, various media content, such as a movie, music, game, advertisement, and shopping items. The content device 10 can be one of various media providers including, but not limited to, a television (TV), personal computer (PC), smart phone, and tablet. The subject may be any human being.

The brainwave detector 100 may measure the brainwave of a subject who is provided with the content through the content device 10. The brainwave detector 100 may then output a measured result associated with the brainwave measurement to the first controller 300. In general, the brainwave detector 100 may be any suitable detector capable of detecting brainwaves.

The bio signal detector 200 may measure bio signals of the subject and may output a measured result associated with the measured bio signal to the first controller 300. In general, the bio signal detector 200 may be any suitable detector capable of detecting bio signals.

The first controller 300 may control the brainwave detector 100 and the bio signal detector 200, and may transmit the brainwave signal received from the brainwave detector 100 and the bio signal received from the bio signal detector 200 to the second controller 400.

In some cases, the first controller 300 can modify the brainwave signals and the bio signals to signal levels available for the second controller 400. For example, in some cases, the first controller 300 can amplify at least one of the brainwave signals and the bio signals before transmitting the signals to the second controller 400. Also, the first controller 300 can output the brainwave signal according to a predetermined bandwidth, for example 0.1 Hz-50 Hz, by filtering, or selectively outputting a part of the brainwave signal. Accordingly, it should be understood that the first controller 300 may include any suitable software and hardware, such as a processor and/or filter, for processing signals received from the brainwave detector 100 and the bio signal detector 200.

The second controller 400 may detect changes (e.g., transitions) in brainwave signals and bio signals before and/or while providing the content through analysis of the brainwave signals and the bio signals received from the first controller 300. The second controller 400 may determine at least one of a degree of engagement and an emotional reaction of the subject to the content based on the changes in the brainwave signals and the bio signals. The second controller 400 may evaluate the content based on the determined results. It should be understood that the second controller 400 may include any suitable software and hardware, such as a processor and/or filter, for processing signals received from the first controller 300. In addition, although FIG. 1 shows the first controller 300 and the second controller 400 as being separate controllers, it should be understood that embodiments of the disclosed subject matter are not limited thereto. For example, in some cases, the first controller 300 and the second controller 400 may be combined into one controller. In some cases, the first controller 300 and the second controller 400 may be formed in more than two controllers.

The camera 500 may take an image of the subject and transmit the image to the second controller 400. In general, the camera 500 may be any suitable image acquisition device capable of obtaining an image of the subject.

Then, the second controller 400 can evaluate the content, in part, by analyzing a movement of the subject from the images provided by the camera 500 and by verifying the determined results, i.e., degree of engagement and emotional reaction, using the analyzed results. Therefore, a reliability of the evaluation of the content can be improved using additional real time information on the subject and comparing the determined results with movement of the subject to remove or correct any inaccuracies. For example, the images of the camera 500 may be synchronized with the bio signals and/or brainwaves, and the images of the camera 500 may be filtered to remove undesired noise, such as, drowsiness, unconscious movements, reflex movements, and the like of test subject, from the measured bio signals and/or brainwaves.

The evaluation standard data storage 600 can be any suitable storage medium, including, for example, an external storage device such as a hard disk or external memory, or an internal memory equipped in a computing device. The evaluation standard data storage 600 may store evaluation standard data for evaluating the content, and may provide the evaluation standard data in response to a request from the second controller 400. The second controller 400 can evaluate an interest-causing level of the content by evaluating the determined results according to the evaluation standard data provided by the evaluation standard data storage 600.

The evaluation standard data may be standardized data representing specific emotional states. For example, the evaluation standard data may represent a common pattern of physical reactions to a same emotional circumstance caused by a same object. An evaluation standard data for "fear" may be obtained by showing a scary movie to a number of subjects and extracting a common pattern of measure signals. However, aspects need not be limited thereto such that the evaluation standard data may be indicative of other emotions, such as happy, sad, anxious, nervous, angry, trust, disgust, anticipation, surprise, etc. The evaluation standard data can be sorted and stored according to various criteria such as a type of content, or age or sex of the subjects. In addition, the second controller 400 can adjust the evaluation standard data as the number of measurements of the content increases, and may control the evaluation standard data storage 600 to store the adjusted evaluation standard data. For example, the second controller 400 can analyze evaluation results of the content accumulated during a certain period to determine whether to adjust the evaluation standards data; can set a new evaluation standards data; and instruct the evaluation standard data storage 600 to store the new evaluation standards data when adjustment of the evaluation standard data is determined to be necessary.

The display 700 is controlled by the second controller 400, and can display an evaluation result from the second controller 400.

Figure 2:
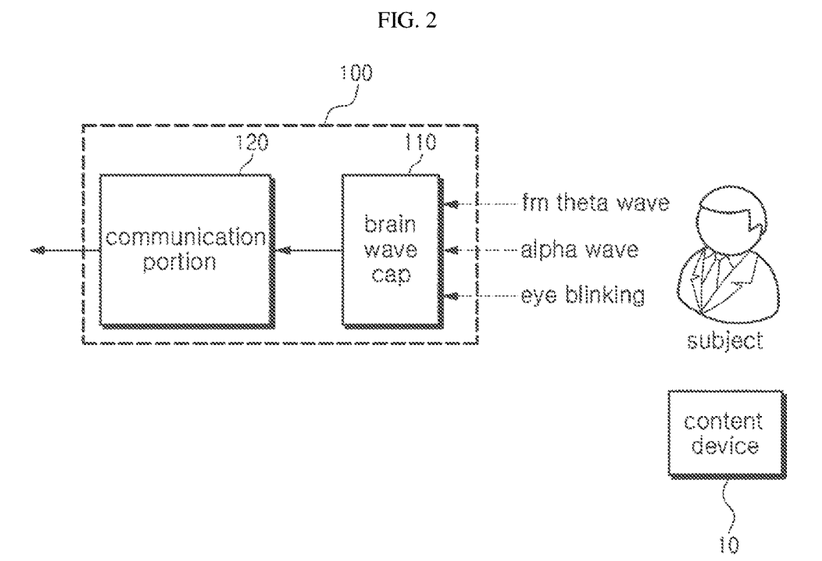
FIG. 2 is a block diagram illustrating a brainwave detector of the content evaluation system according to exemplary embodiments of the present disclosure.
Figure 3:
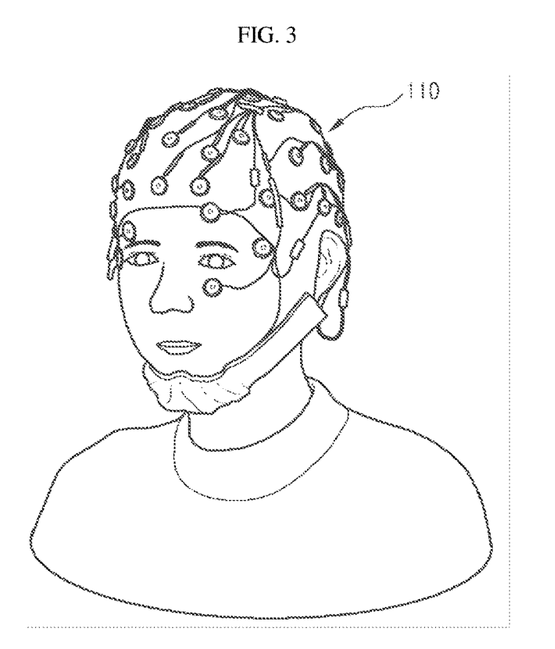
FIG. 3 is a drawing illustrating a brainwave cap of the brainwave detector worn on a head of a subject according to exemplary embodiments of the present disclosure.

FIG. 2 is a block diagram illustrating a brainwave detector 100 of the content evaluation system, according to exemplary embodiments of the disclosed subject matter. FIG. 3 is a drawing illustrating a brainwave cap 110 of the brainwave detector 100 worn on a head of the subject, according to exemplary embodiments of the disclosed subject matter.

Referring to FIG. 2 and FIG. 3, the brainwave signal detected by the brainwave detector 100 may include at least one of frontal midline theta wave and alpha wave. The frontal midline theta wave is a brainwave within a range of 6.5 Hz-7.5 Hz, and the alpha wave is a brainwave within a range of 8 Hz-12 Hz.

The brain detector 100 may include a brainwave cap 110 worn on a head of a subject to measure and detect brainwaves, and a transceiver 120 to transmit the brainwave signal received from the brainwave cap 110 to the first controller 300.

The brainwave cap 110 can consist of a plurality of electrodes which contact various positions of the head of the subject. The electrodes may contact a forehead of the subject and a face of the subject, including near (e.g., below, above, on the side of) the eyes of the subject to detect eye blinking of the subject.

The transceiver 120 may transmit brainwave signals, such as the frontal midline theta wave and the alpha wave, and a signal corresponding to a blinking eye provided from the brainwave cap 110 to the first controller 300. The brainwave signal transmitted by the transceiver 120 may selectively include one or more types of brainwaves, e.g., frontal midline theta wave and alpha wave.

The second controller 400 may analyze the brainwave signal. Before analyzing the brainwave signal, the reliability of the analysis of the brainwave signal may be improved by transforming the brainwave as follows. First, noise included in the brainwave signal may be removed. Such noise canceling can be performed not only by human visual inspection but also by the first controller 300 or the second controller 400 automatically. Second, the brainwave signal may be filtered so that only a certain bandwidth (e.g., 0.1 Hz-50 Hz) passes the filter. Third, a component related to the blinking eye can be eliminated from the brainwave signal through an independent component analysis. Fourth, a fast Fourier transformation (FFT) for the brainwave signal before and while the content is provided can be performed. Fifth, the frontal midline theta wave and the alpha wave highly related to a degree of engagement (i.e., concentration) may be extracted by sorting the brainwave signal according to frequency. The second controller 400 may perform the removal of the blinking eye component, the fast Fourier transformation process, and the brainwave extracting process.

A degree of engagement by the subject with the content may be determined to have increased when an amplitude magnitude of the frontal midline theta wave increases and the eye blinking per minute rate decreases. Therefore, the second controller 400 can determine the degree of engagement by the subject with the content by monitoring changes of the frontal midline theta wave, the alpha wave, and the eye blinking per minute rate.

Figure 4:
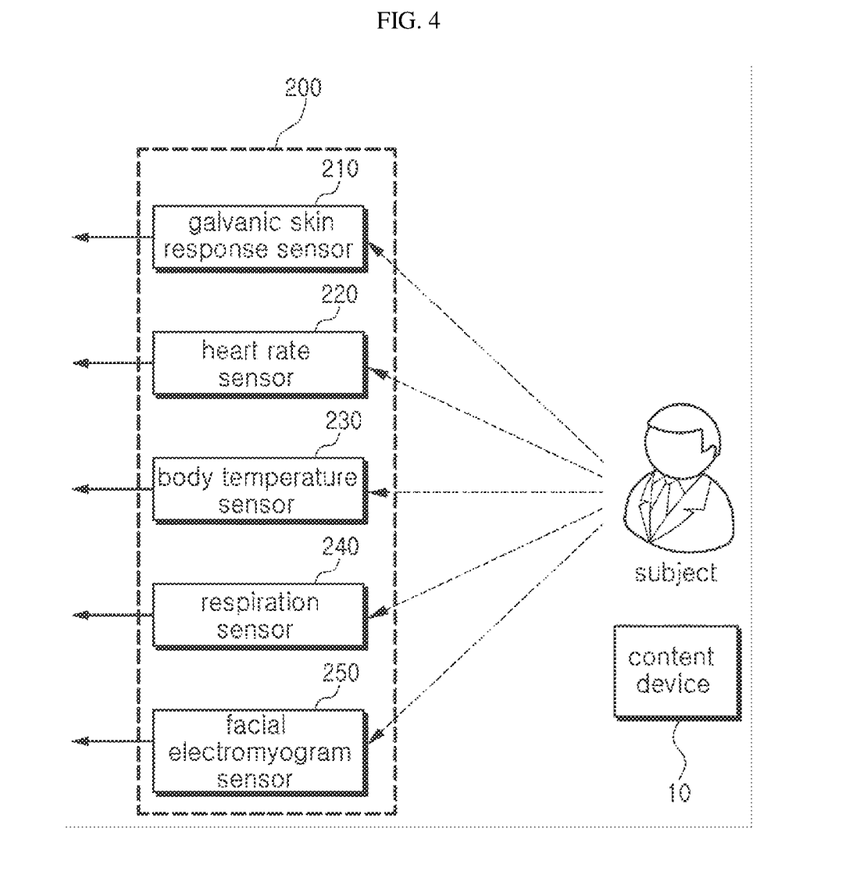
FIG. 4 is a block diagram illustrating a bio signal detector of the content evaluation system according to exemplary embodiments of the present disclosure.

FIG. 4 is a block diagram illustrating a bio signal detector 200 of the content evaluation system, according to exemplary embodiments of the disclosed subject matter.

Referring to FIG. 4, the bio signal measured by the bio signal detector 200 may include at least one of a Galvanic skin response, heart rate, body temperature, respiration, and facial electromyogram.

The bio signal detector 200 may include a Galvanic skin response sensor 210 to measure the Galvanic skin response of the subject, a heart rate sensor 220 to measure a heart rate of the subject, a body temperature sensor 230 to measure a body temperature of the subject, a respiration sensor 240 to measure a respiration of the subject, and a facial electromyogram sensor 250 to measure a facial electromyogram.

The second controller 400 may determine the degree of engagement and an emotional reaction of the subject to the content through changes in the bio signals measured by the bio signal detector 200. For example, the second controller 400 may determine the degree of engagement of the subject to the content through changes in the Galvanic skin response, the heart rate, the body temperature, and the respiration of the subject, and may determine the emotional reaction, i.e., positive emotion or negative emotion, of the subject to the content through changes in the facial electromyogram of the subject.

The degree of engagement of the subject to the content is determined as increasing when the Galvanic skin response decreases, the heart rate increases, the body temperature decreases, and the respiration decreases.

The second controller 400 may therefore determine the degree of engagement of the subject to the content based on changes in Galvanic skin response, changes in the heart rate, changes in the body temperature, changes in the respiration, changes in the frontal midline theta wave and the alpha wave, and changes of the eye blinking per minute rate. For example, as shown in Table 1, compared to a normal, baseline, or stable state, skin conductivity (Galvanic skin response) may be increased, body temperature may be decreased, heart rate may be increased, breathing may be decreased, eye-blinking may be decreased, and the frontal midline theta wave may be increased to indicate that the subject is engaged. Further, as shown in Table 1, compared to a normal, baseline, or stable state, skin conductivity (Galvanic skin response) may be decreased, body temperature may be increased, heart rate may be decreased, breathing may be increased, eye-blinking may be maintained or unchanged, and the frontal midline theta wave may be maintained or unchanged to indicate that the subject is not engaged.

TABLE 1

Measured Bio Signal Changes Indicating Engagement

| Measured Bio Signal | Change with respect to normal state of subject | |
| --- | --- | --- |
| | Indicates Engaged | Indicates not Engaged |
| skin conductivity | increased | decreased |
| body temperature | decreased | increased |
| heart rate | increased | decreased |
| breathing | decreased | increased |
| eye-blinking | decreased | maintained |
| frontal midline theta wave | increased | maintained |

Figure 5:
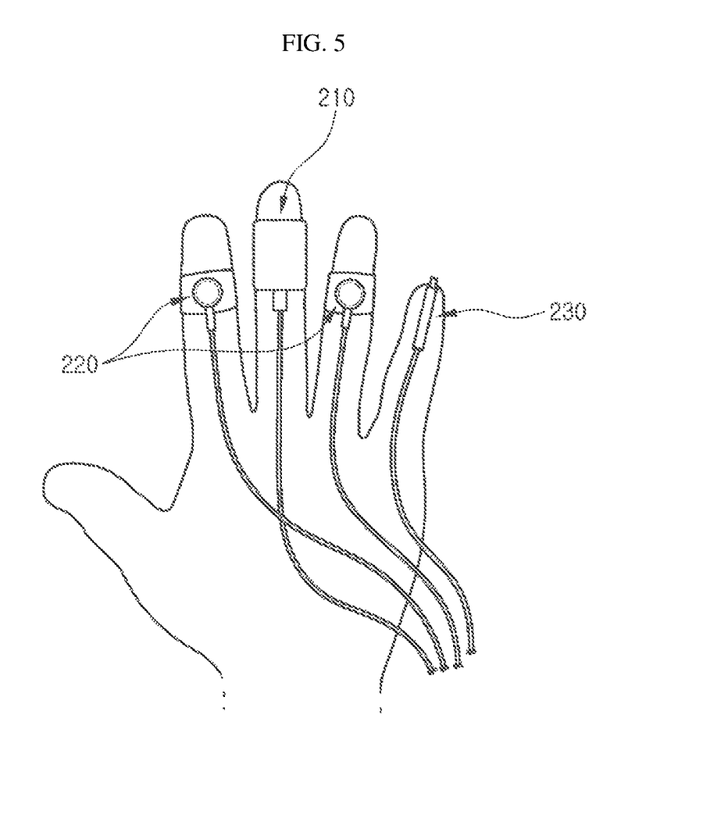
FIG. 5 is a drawing illustrating the Galvanic skin response sensor, the heart rate sensor, and the body temperature sensor attached to fingers of the subject, according to exemplary embodiments of the present disclosure.

FIG. 5 illustrates a Galvanic skin response sensor 210, a heart rate sensor 220, and a body temperature sensor 230 attached to fingers of a subject, according to exemplary embodiments of the disclosed subject matter.

Referring to FIG. 5, the Galvanic skin response sensor 210, the heart rate sensor 220, and the body temperature sensor 230 may be attached to fingers of the subject. In some cases, the Galvanic skin response sensor 210, the heart rate sensor 220, and the body temperature sensor 230 may be attached to a middle finger, index finger and ring finger, and a little finger, respectively. Each of the sensors 210, 220, and 230 may measure a corresponding bio signal, as noted above.

In some cases, the Galvanic skin response sensor 210, the heart rate sensor 220, and the body temperature sensor 230 may be attached to body parts other than fingers. For example, when the subject is a gamer playing a PC game content, the Galvanic skin response sensor 210, the heart rate sensor 220, and the body temperature sensor 230 can be attached to toes of the subject.

Figure 6:
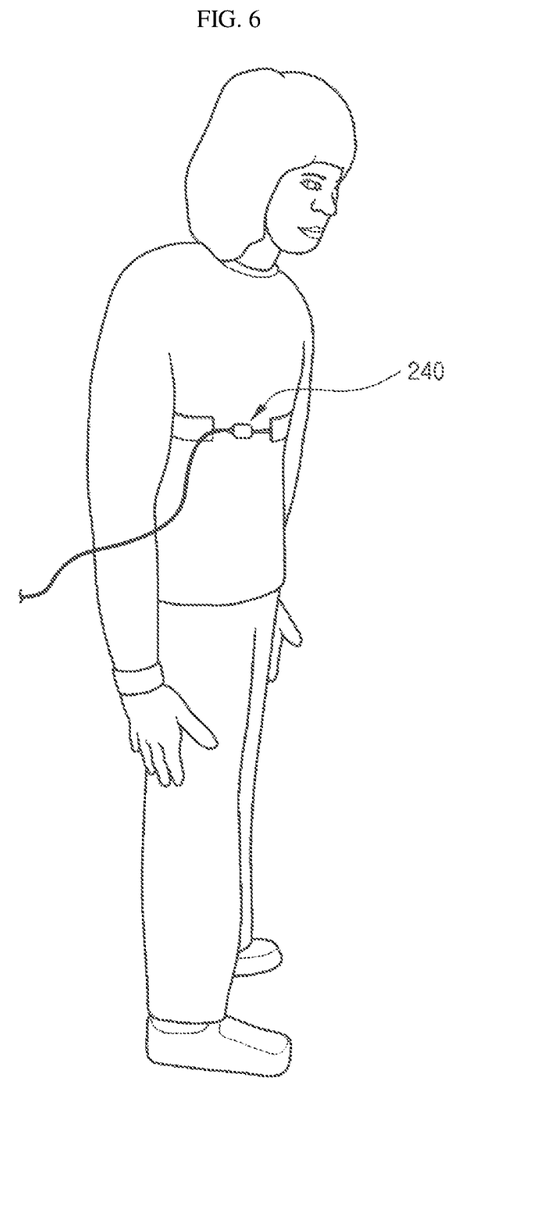
FIG. 6 is a drawing illustrating a respiration sensor of the bio signal detector attached to the subject, according to exemplary embodiments of the present disclosure.

FIG. 6 is a drawing illustrating a respiration sensor of the bio signal unit attached to the subject, according to exemplary embodiments of the disclosed subject matter.

Referring to FIG. 6, the respiration sensor 240 may be attached to the subject's chest. However, the respiration sensor 240 may be attached to any other body part where respiration can be measured.

Figure 7:
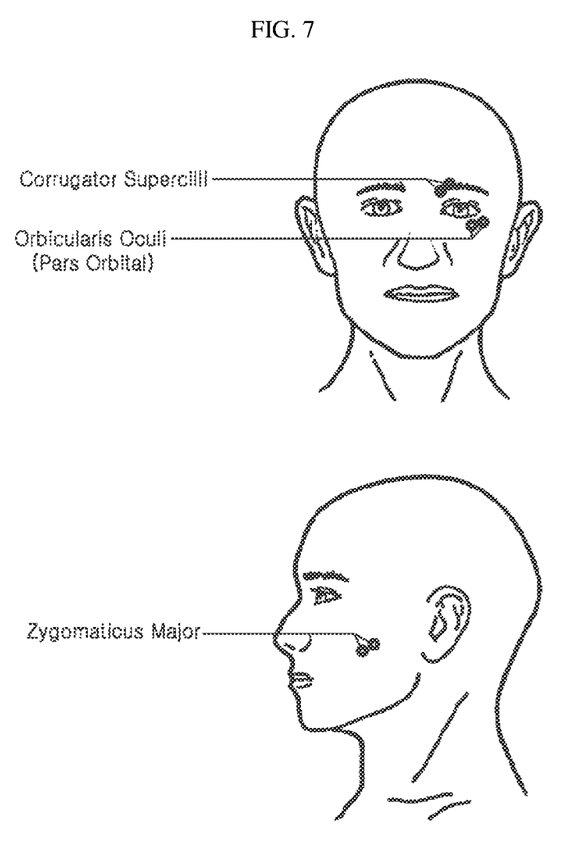
FIG. 7 illustrates the location of facial electromyogram sensors on a face of the subject, according to exemplary embodiments of the present disclosure.

FIG. 7 illustrates locations of the facial electromyogram sensors on a face of the subject, according to exemplary embodiments of the disclosed subject matter.

Referring to FIG. 7, the facial electromyogram sensor 250 can include at least one measurement of Corrugator Supercilii, Orbicularis Oculi, and Zygomaticus Major to detect a facial electromyogram.

The facial electromyogram sensor 250 may include a first facial electromyogram sensor to monitor the Corrugator Supercilii, a second facial electromyogram sensor to monitor the Orbicularis Oculi, and a third facial electromyogram sensor to monitor the Zygomaticus Major.

The second controller 400 can determine an emotional reaction of the subject to the content through changes in the facial electromyogram of the subject. For example, the second controller 400 may determine a negative emotional reaction through measurements of the Corrugator Supercilii, and determine a positive emotional reaction through measurements of the Orbicularis Oculi and Zygomaticus Major. The positive emotional reaction may be a positive element or factor in evaluating the content, and the negative emotional reaction may be a negative element or factor in evaluating the content. A weight of the facial electromyogram may be given to each facial muscle measured to evaluate the emotional reaction more precisely.

Hereinafter, a method evaluating content using the content evaluation system is described.

Figure 8:
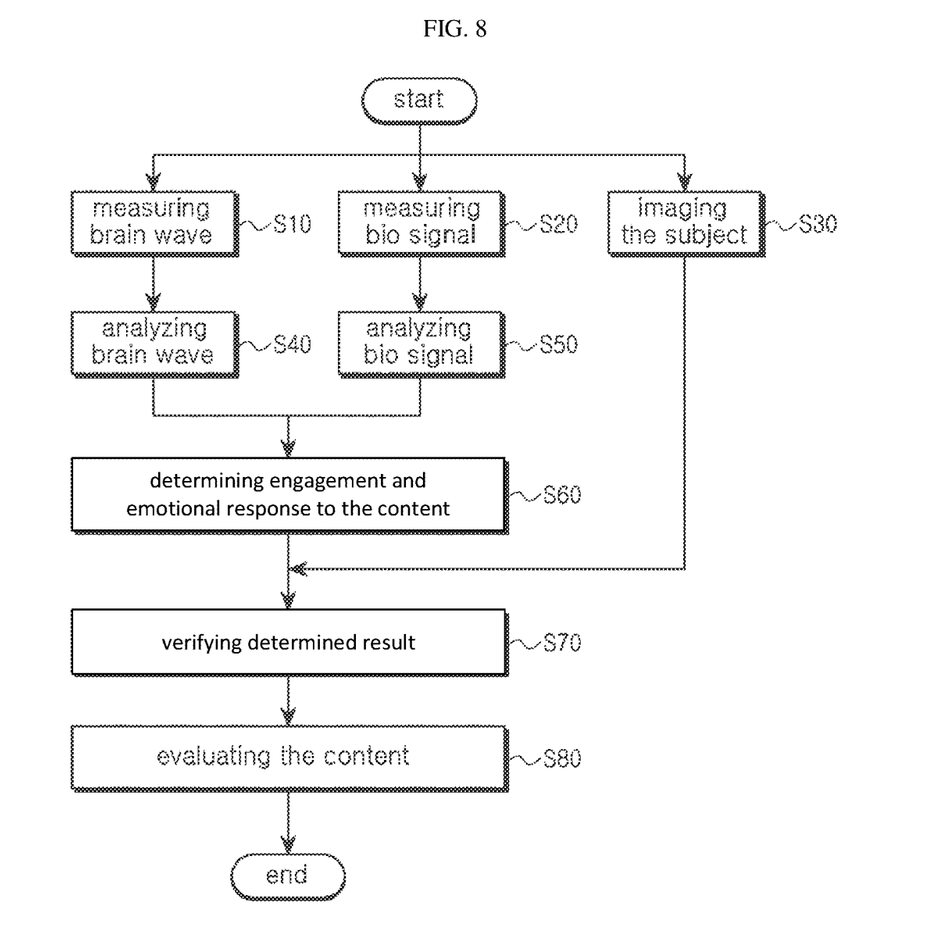
FIG. 8 is a flow chart illustrating a content evaluation method according to exemplary embodiments of the present disclosure.

FIG. 8 is a flow chart illustrating a content evaluation method according to exemplary embodiments of the disclosed subject matter.

Referring to FIG. 8, a content evaluation method may include measuring a brainwave signal of a subject provided with the content using the brainwave detector 100 S10; measuring bio signals of the subject using the bio signal detector 200 S20; and obtaining an image of the subject though the camera 500 S30. In some cases, S10, S20, and S30 may be performed simultaneously, and, in some cases, they may be performed in a different order.

The brainwave signal measured by the brainwave detector 100 may include at least one of a frontal midline theta wave or an alpha wave. An eye blinking rate of the subject may be measured as part of the brainwave signal. The bio signal measured by the bio signal detector 200 may include at least one of a Galvanic skin response, a heart rate, a body temperature, a respiration, and a facial electromyogram. The facial electromyogram may include at least one electromyogram measurement of Corrugator Supercilii, Orbicularis Oculi, and Zygomaticus Major.

After measuring the brainwave signal S10 and the bio signal S20, the brainwave signal may be analyzed S40 by the second controller 400 to detect changes in the brainwave before and while content is provided. In addition, the second controller 400 may analyze the bio signal to detect changes of the bio signal before and while the content is provided S50. S40 and S50 may be performed independently or simultaneously.

In some cases, determining of the changes in the brainwave signal S40 may be performed by an independent component analysis that removes eye-blink artifacts from the brainwave signal measurement result.

Subsequently, the second controller 400 may determine the subject's engagement and emotional reaction to the content by using the changes in the brainwave signal and the bio signal S60.

Changes in the brainwave signal may correspond to the degree of engagement to the content. For example, the degree of engagement of the subject to the content may be determined as increasing when an amplitude magnitude of the frontal midline theta wave increases and the eye blinking per minute rate decreases.

In addition, changes of the bio signal may affect the degree of engagement and emotional reaction of the subject to the content. For example, the degree of engagement to the content may be determined from changes of the Galvanic skin response, the heart rate, the body temperature, and the respiration of the subject. The emotional reaction of the subject to the content may be determined from changes of the facial electromyogram of the subject.

In some cases, the degree of engagement of the subject to the content is determined as increasing when the Galvanic skin response decreases, the heart rate increases, the body temperature decreases, and the respiration decreases. In some cases, the emotional reaction of the subject to the content may be determined as a negative emotional reaction through the measurement of Corrugator Supercilii, and a positive emotional reaction may be determined through the measurement of Orbicularis Oculi and Zygomaticus Major.

Then, the second controller 400 may verify the determined result using an image of the subject obtained by the camera 500. For example, the second controller 400 may evaluate the content after analyzing overall movement of the subject from images provided by the camera 500 and may then verify the determined results, i.e., degree of engagement and emotional reaction, using the analyzed results. For example, the images of the camera 500 may be synchronized with the bio signals and/or brainwaves, and the images of the camera 500 may be filtered to remove undesired noise, such as, drowsiness, unconscious movements, reflex movements, and the like of test subject, from the measured bio signals and/or brainwaves. Therefore, a reliability of the evaluation of the content can be improved because errors can be removed, corrected, and complemented by verifying the determined results through a comparison with the overall movement of the subject.

After S70, the second controller 400 may evaluate the content S80 using the verified result. The step of evaluating the content may be performed according to an evaluation standard data provided by the evaluation standard data storage 600. The evaluation standard data can be sorted and stored according to a type of the content or age or sex of the subjects, and may be updated through analysis of accumulated evaluation data.

The content evaluation result may be displayed on the display 700.

According to exemplary embodiments of the disclosed subject matter, more reliable box-office prediction can be achieved through content evaluation using objective data such as brainwave, bio-signals and images of the subject provided with a cultural content. The disclosed content evaluation system and method may allow content providers to improve portions of their content that were not liked by subjects and to correct or modify these portions. For example, the portions of the contents may be modified or corrected by replacing the portion, for example a scene, a character, a scenario, music, story, or other portion of contents, having data associated therewith that is interpreted as the subjects being not interested in or not engaged with that portion. Also, the content evaluation system and method can provided a quantitative and qualitative evaluation of contents to content providers to improve a quality of the content.

It will be apparent to those skilled in the art that various modifications and variations can be made in the present disclosure without departing from the spirit or scope of the disclosed subject matter. Thus, it is intended that the present disclosure cover the modifications and variations of the disclosed subject matter provided they come within the scope of the appended claims and their equivalents.

What is claimed is:

1. A method of evaluating media content, the method comprising:
    sorting and storing evaluation standard data in a database according to a criteria comprising at least one of type of a media content, age of a subject, or sex of the subject;
    exposing the subject to the media content at a second time;
    detecting a brainwave signal of the subject at a first time and at the second time with a brainwave detector cap worn on the subject's head;
    detecting a bio signal of the subject at the first time and at the second time, wherein the bio signal includes a facial electromyogram and at least one of a galvanic skin response, a heart rate, a body temperature, or a respiration of the subject;
    obtaining images of the subject at the first time and at the second time; and
    receiving the brainwave signal detected at the first time, the bio signal detected at the first time, and the image obtained at the first time with a controller;
    receiving the brainwave signal detected at the second time, the bio signal detected at the second time, and the image obtained at the second time with the controller;
    determining a change in the brainwave signal between the first time and the second time, with the controller;
    determining a change in the bio signal between the first time and the second time, with the controller;
    determining a degree of engagement and a degree of an emotional reaction of the subject to the content using the change in the brainwave signal and the change in the bio signal, with the controller;
    analyzing a movement of the subject from the images of the subject at the first time and at the second time to provide analyzed results, with the controller;

verifying the determined degree of engagement and the emotional reaction of the subject using the analyzed results, including removing motion noise due to drowsiness, unconscious movements or reflex movements from the brainwave signal and the bio signal, with the controller;

evaluating the content exposed to the subject at the second time based on the degree of the engagement and the emotional reaction according to the evaluation standard data that is stored in the database, with the controller; and updating the evaluation standard data stored in the database based on the step of evaluating the content.

2. The method of claim 1,
wherein the brainwave signal comprises at least one of a frontal midline theta wave or an alpha wave.

3. The method of claim 1, wherein detecting the brainwave signal comprises:
measuring the brainwave signal of the subject; and
measuring a blinking of an eye of the subject.

4. The method of claim 3,
wherein determining the change of the brainwave signal comprises removing eye-blink artifacts from a result of the measured brainwave signal.

5. The method of claim 3,
wherein the degree of the engagement of the subject is determined as increasing when an amplitude magnitude of the frontal midline theta wave increases and an eye blinking per minute rate decreases.

6. The method of claim 1, wherein determining the degree of the engagement and the emotional reaction comprises:
determining the degree of engagement through changes of the Galvanic skin response, the heart rate, the body temperature, and the respiration of the subject; and
determining the emotional reaction through a change of the facial electromyogram of the subject.

7. The method of claim 6,
wherein the facial electromyogram comprises at least one measurement of a Corrugator Supercilii, Orbicularis Oculi, and Zygomaticus Major.

8. The method of claim 7, further comprising:
determining a negative emotional reaction of the subject through the measurement of Corrugator Supercilii; and
determining a positive emotional reaction of the subject through the measurement of the Orbicularis Oculi and the Zygomaticus Major.

9. The method of claim 6,
wherein the degree of the engagement is determined as increasing when the Galvanic skin response decreases, the heart rate increases, the body temperature decreases, and the respiration decreases.

* * * * *